United States Patent
Perry

(10) Patent No.: US 7,097,661 B2
(45) Date of Patent: Aug. 29, 2006

(54) VENTILATION TUBE FOR A MIDDLE EAR

(75) Inventor: Christopher Francis Perry, Camp Hill (AU)

(73) Assignee: Perry Microtube Pty Ltd, (AU)

( * ) Notice: Subject to any disclaimer, the term of this patent is extended or adjusted under 35 U.S.C. 154(b) by 489 days.

(21) Appl. No.: 10/168,103

(22) PCT Filed: Aug. 3, 2001

(86) PCT No.: PCT/AU01/00949

§ 371 (c)(1),
(2), (4) Date: Jun. 12, 2002

(87) PCT Pub. No.: WO03/013361

PCT Pub. Date: Feb. 20, 2003

(65) Prior Publication Data

US 2003/0187456 A1    Oct. 2, 2003

(51) Int. Cl.
*A61F 2/18* (2006.01)
*A61F 11/00* (2006.01)
*A61M 31/00* (2006.01)

(52) U.S. Cl. .................. 623/10; 604/285; 606/109
(58) Field of Classification Search .............. 623/12; 606/107, 108, 109; 604/285; D24/173
See application file for complete search history.

(56) References Cited

U.S. PATENT DOCUMENTS

| | | | |
|---|---|---|---|
| 3,807,409 A | 4/1974 | Paparella et al. |
| 3,871,380 A | 3/1975 | Heros |
| 4,174,716 A | 11/1979 | Treace |
| D274,753 S | 7/1984 | Armstrong |
| 4,468,218 A | 8/1984 | Armstrong |
| 4,650,488 A | 3/1987 | Bays et al. |
| 4,695,275 A | 9/1987 | Bruce et al. |
| 4,744,792 A | 5/1988 | Sander et al. |
| 4,764,168 A | 8/1988 | Suh |
| 4,775,370 A | 10/1988 | Berry |
| 4,808,171 A | 2/1989 | Berger |
| 5,026,378 A | 6/1991 | Goldsmith, III |
| 5,053,040 A | 10/1991 | Goldsmith, III |
| 5,137,523 A | 8/1992 | Peerless et al. |
| 5,178,623 A | 1/1993 | Cinberg et al. |
| 5,207,685 A | 5/1993 | Cinberg et al. |
| 5,389,088 A | 2/1995 | Hageman |
| 5,466,239 A | 11/1995 | Cinberg et al. |
| D371,606 S | 7/1996 | Doyle |
| 5,649,932 A | 7/1997 | Fouin et al. |
| 5,827,295 A | 10/1998 | Del Rio et al. |
| 6,042,574 A | 3/2000 | O'Halloran |

FOREIGN PATENT DOCUMENTS

| | | |
|---|---|---|
| GB | 2 316 319 | 2/1998 |
| SE | 7904 288 | 5/1979 |

OTHER PUBLICATIONS

Smith & Nephew, Commitment Development Enhancement, "First In MyringoTomy," Mar. 1999, pp. 1-3.

*Primary Examiner*—David J. Isabella
(74) *Attorney, Agent, or Firm*—Cantor Colburn LLP

(57) ABSTRACT

A ventilation tube has a tubular member with generally circular flanges at opposite ends. Each flange has a respective tab that is angled obliquely to the axis of the tubular member. The tabs are diametrically opposite, and angled in opposite senses. Each tab has straight non-cutting edges tangential to its associated flange, and an arcuate nose portion. Each flange (may be used either for grasping the ventilation tube, or for insertion into an incision in a tympanic membrane, thereby permitting the ventilation tube to be used reversibly.

12 Claims, 2 Drawing Sheets

VENTILATION TUBE FOR A MIDDLE EAR

This invention relates to an improved ventilation tube for a middle ear. In particular, the invention is directed to a ventilation tube which can be inserted into a patient's tympanic membrane (eardrum) in either of two opposite orientations.

BACKGROUND ART

Many persons, particularly children, suffer from accumulation of fluid in the middle ear. In a surgical operation, known as a myringotomy or tympanostomy, an incision is made in the tympanic membrane or eardrum to ventilate the middle ear and/or drain the fluid. This simple incision in the tympanic membrane may provide temporary relief, but incisions of the eardrum normally self-heal within a relatively short time. For ventilation/drainage for longer periods, after myringotomy the surgeon inserts a ventilation tube or "grommet" through the incision, thereby providing a vent which equalises the pressure on either side of the eardrum, and allows fluid to be drained from the middle ear. The eardrum soon heals around the waist of the grommet, which is subsequently expelled from the eardrum usually some months later leaving an intact eardrum.

To insert the ventilation tube into the incision in the tympanic membrane, the ear surgeon grasps the tube with a special grasping forceps, and manoeuvres the tube into position. As the ventilation tube is extremely small, typically less than a few millimetres in diameter, and as the tympanic membrane is so delicate, the surgeon must exercise considerable skill and dexterity in the operation.

The ventilation tube is typically in the form of a short tubular conduit having radial flanges at its opposite ends which locate on opposite sides of the tympanic membrane and assist in keeping the ventilation tube in place. (The eardrum has a natural tendency to dislodge the ventilation tube from the incision as it heals). Various designs have been used or proposed for ventilation tubes in order to facilitate their insertion after a myringotomy and the shape and design of the grommet will influence the length of time they are retained within the drum. Many ventilation tubes have a tab extending from an end flange to enable the ventilation tube to be grasped more easily. Examples of such ventilation tubes can be found in U.S. Pat. Nos. 3,807,409; 3,871,380; 4,174,716; 4,650,488; 4,695,275; 4,764,168; 5,137,523; 5,649,932 and 6,042,574. The tabs of the known ventilation tubes generally extend parallel or perpendicularly to the axis of the tube.

It has been found that insertion of the ventilation tube is facilitated if the leading portion of the tube is inserted into the incision in the tympanic membrane at an angle. Known ventilation tubes which have grasping tabs orientated either parallel or perpendicularly to the longitudinal axis of the tube do not place the tube in the preferred orientation for insertion. The surgeon must therefore manoeuvre the grasping forceps to angle the ventilation tube, increasing the difficulty of the operation.

U.S. Pat. Nos. 5,178,623 and 5,207,685 disclose ventilation tubes having grasping tabs angled obliquely to the axis of the tube. The ventilation tube of U.S. Pat. No. 5,178,623 has a cutting edge at the opposite end of the tube from the grasping tab, diametrically opposite to the tab. In use, the surgeon holds the grasping tab with forceps and presses the ventilation tube against the tympanic membrane, firstly to perforate it with the cutting edge, and then to insert the cutting edge and its associated flange through the incision to seat the ventilation tube in the membrane.

The ventilation tubes of U.S. Pat. No. 5,178,623 may permit the incision and insertion steps to be performed by the same instrumentation, namely the ventilation tube itself, but the provision of a cutting edge on the ventilation tube introduces added risk. The cutting edge must be sharp as it is intended to perform the initial perforation of the eardrum. As a myringotomy knife, the ventilation tube, when grasped with forceps by the surgeon, would not be as stable as a regular myringotomy knife, particularly for very thin and flaccid eardrums and excessively thick eardrums. The cutting edge would therefore appear to be less useful to a surgeon, and possibly more traumatic if the cutting edge inadvertently scratches the skin of the external canal of the ear and/or the drum and medial wall lining of the middle ear, resulting in bleeding and unnecessary injury. Thus, rather than facilitating the insertion of the ventilation tube, the provision of the cutting edge on the tube requires greater skill and dexterity by the ear surgeon.

The ventilation tube of U.S. Pat. No. 5,207,685 also poses the risk of trauma from its sharp cutting edge. Moreover, this ventilation tube must be removed after the incision, released by the forceps, and then re-grasped on a second grasping tab for insertion. The ventilation tube is considered unnecessarily complicated and difficult for surgeons and theatre nurses to use.

A significant disadvantage of the ventilation tubes of U.S. Pat. Nos. 5,178,623 and 5,207,685, as well as the ventilation tubes of the other patents identified above, is that they are designed for use in one orientation only. Thus, when picking up the tiny ventilation tubes, the theatre nurse or surgeon must ensure that the tubes are grasped at the correct end. The tubes may need to be moved around to correctly orientate the tab for grasping by the forceps.

U.S. design Pat. No. D371606 shows an ear ventilation tube which appears to be reversible, but the tabs of the illustrated ventilation tube are small and therefore difficult to grasp. Such small tags, if they are designed to aid insertion are very small and their sides do not meet the outer circumference of the flange tangentially. Thus, if this small tag is able to engage a preformed incision in the tympanic membrane, advancement of the grommet will cause it to be pushed bluntly onto the ends of the preformed incision. The grommet will not slide smoothly to widen the preformed incision resulting possibly in excessive force, a sudden give or tear in the eardrum and the resulting hole possibly being too big to hold the grommet within its space.

Moreover, the tabs are orientated parallel to the longitudinal axis of the tube, and hence the tube is not held at the desired orientation by the grasping forceps. The flanges of the ventilation tube of U.S. design Pat. No. D371606 are also angled obliquely to the axis of the tube, which tends to locate the tube at an angle to the eardrum. Such skewed seating of the tube may facilitate dislodgement of the tube from the eardrum.

It is an object of this invention to provide an improved ventilation tube which is reversible, i.e. it may be used in either of two orientations, safe to use, and configured for easy insertion in a tympanic membrane.

SUMMARY OF THE INVENTION

In one broad form, the invention provides a ventilation tube suitable for insertion in an incised tympanic membrane, the ventilation tube comprising a tubular member having a longitudinal axis, a first flange located at one end of the tubular member and having a first tab extending therefrom, and a second flange located at the opposite end of the tubular member and having a second tab extending therefrom, the second tab being located diametrically opposite to the first tab. Both of the first and second tabs are angled obliquely to the longitudinal axis of the tubular member and are able to be grasped by forceps in use. Both of the first and second tabs also have non-cutting edges suitable for insertion in an incision in the tympanic membrane. In this manner, the ventilation tube may be used reversibly. That is, either the first or second tab may be grasped by the forceps, and the other tab used for insertion in the tympanic membrane.

Each tab is typically a tongue, tag or other integrally-formed extension of its respective flange.

The first and second flanges are preferably perpendicular to the longitudinal axis of the tubular member. The first and second tabs are angled to the plane of their respective associated flanges preferably by approximately equal angles, but in opposite senses, so that the first and second tabs are generally parallel. Each tab is typically angled between 15° and 60° to the plane of its respective flange, and preferably about 30°.

Each tab preferably is of "blunt arrowhead" shape, comprising a pair of substantially straight edges angled to each other and tangential to its associated flange, and a nose portion with an arcuate edge extending between the substantially straight edges. This shape facilitates insertion of the tab through the incision in the tympanic membrane.

The invention also provides a method of using the above-described ventilation tube, comprising the steps of forming an incision in the tympanic membrane, grasping either one of the first and second tabs with forceps, using the forceps to insert the other of the first and second tabs into the incision, and pushing the other tab and its associated flange through the incision, to thereby seat the ventilation tube in the membrane with the first and second flanges on opposite sides thereof.

The incision may have an initial length shorter than the diameter of the flange associated with the other tab. As the other tab is pushed into the membrane, it stretches or widens the incision just enough to accommodate the passage of the tab and its associated flange therethrough, thereby resulting in a snug fit for the ventilation tube in the membrane.

In order that the invention may be more fully understood and put into practice, a preferred embodiment thereof will now be described by way of example, with reference to the accompanying drawings.

DESCRIPTION OF PREFERRED EMBODIMENT

Figure 1:
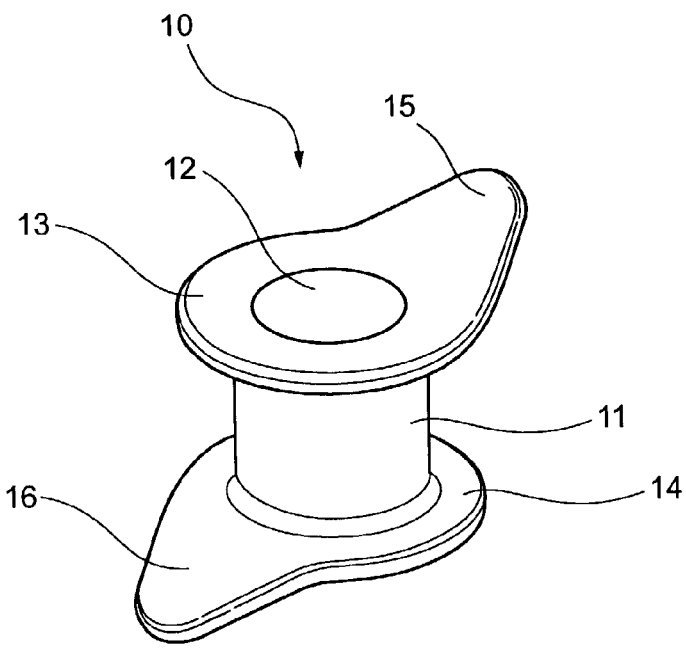
FIG. 1 is a perspective view of a ventilation tube according to a preferred embodiment of the invention.
Figure 4:
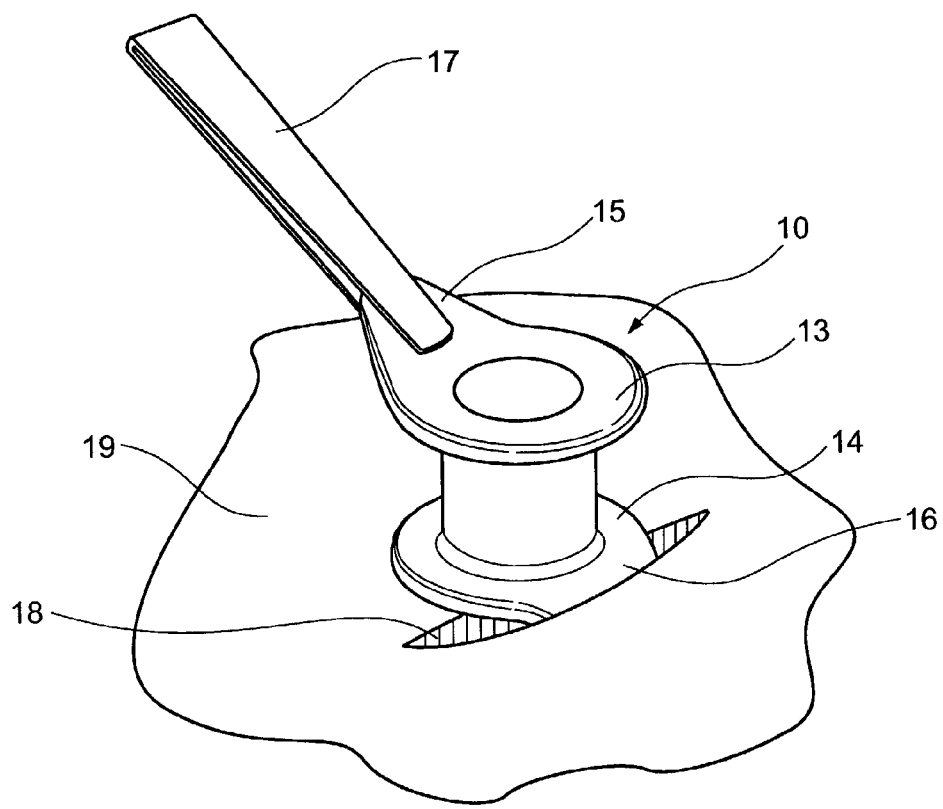
FIG. 4 is a perspective view illustrating insertion of the ventilation tube of FIG. 1 in a tympanic membrane.
Figure 2:
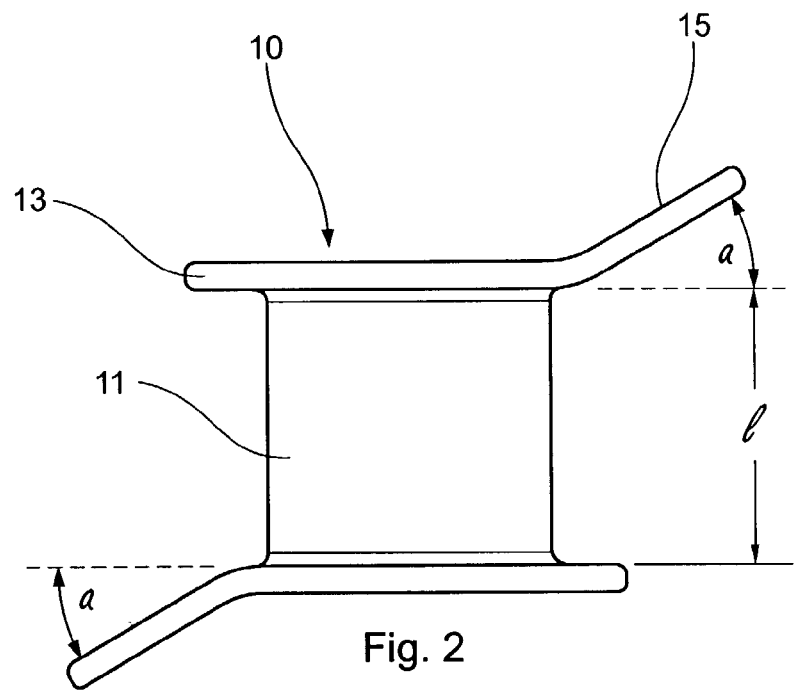
FIG. 2 is an elevation of the ventilation tube of FIG. 1.
Figure 3:
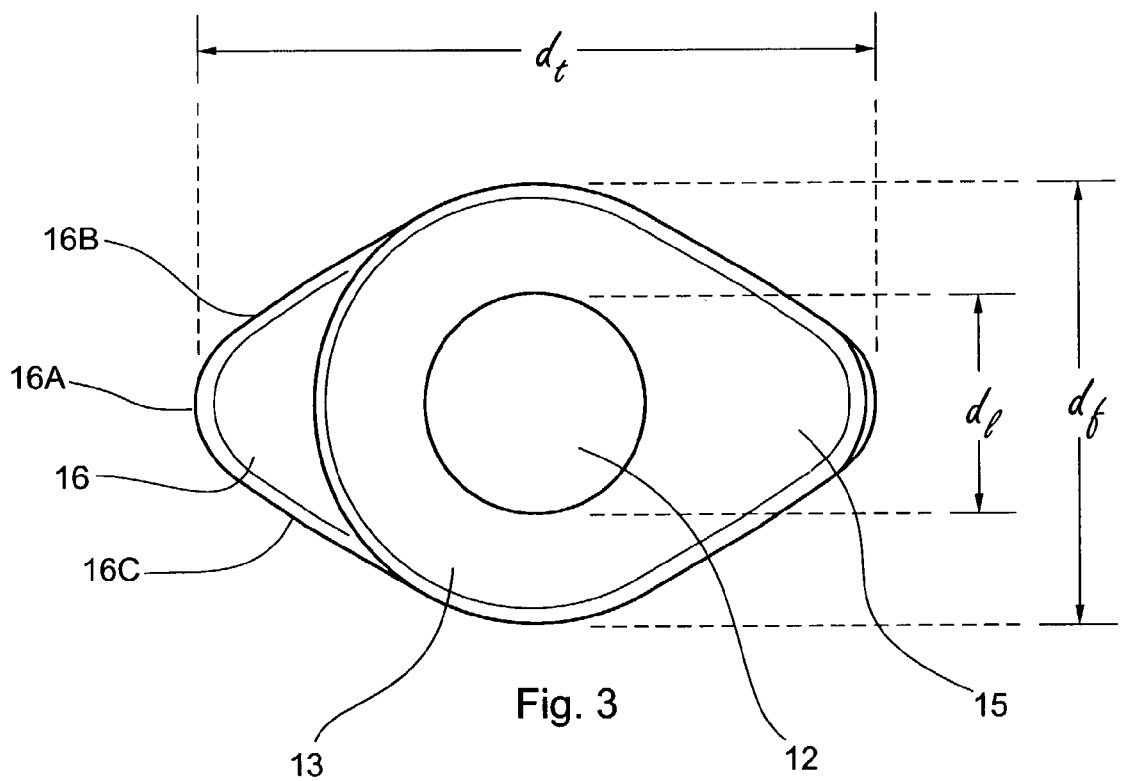
FIG. 3 is a plan view of the ventilation tube of FIG. 1.

As shown in FIGS. 1 to 3, a tympanic ventilation tube 10, also known as a grommet, is in the form of a tubular member 11 having a bore 12 therethrough defining a lumen. In use, the ventilation tube 10 is inserted in an incision in a tympanic membrane or eardrum so that the lumen 12 provides a duct or channel for draining fluid from the middle ear and/or ventilating the middle ear space via the external auditory canal.

The tubular member 11 is provided with generally circular flanges 13, 14 at its opposite ends, each flange being orientated substantially perpendicularly to the axis of the tubular member 11. The flanges 13, 14 serve to retain the ventilation tube in the tympanic membrane. More particularly, by orientating the flanges 13, 14 perpendicularly to the axis of the tubular member 11, they provide greater resistance to the tendency of the eardrum to dislodge the ventilation tube therefrom as the incision heals.

Each flange 13, 14 has an integrally-formed extension in the form of a tongue, tag or tab 15, 16, respectively. Tabs 15, 16 are located on diametrically opposite sides of their respective flanges 13, 14, and are generally of the same shape and size.

The tabs 15, 16 are angled obliquely to the axis of the tubular member 11 by being angled out of the plane of their respective associated flanges 13, 14. As shown in FIG. 2, each tab 15, 16 is angled at an angle "a" to the plane of its respective flange 13, 14. Typically, angle "a" is between 15° and 60°, and preferably around 30°. The tabs 15, 16 are angled to their respective flanges in the opposite direction, and hence are approximately in parallel planes.

Each tab 15, 16 has blunt or otherwise non-cutting edges which comprise a pair of straight edge segments on either side of an arcuate edge portion. More specifically, as illustrated in FIG. 3 with reference to tab 16, the tab has a "blunt arrowhead" shape comprising a nose portion with an arcuate non-cutting distal edge 16A between a pair of straight edges 16B, 16C which are tangential to the flange 14. (Tab 15 has a substantially identical construction at the diagonally opposite end of the ventilation tube 10).

The ventilation tube is typically made from a stiff material such as TEFLON™, or metal such as gold or titanium or an alloy thereof.

The ventilation tube 10 may be made in different sizes to suit particular applications. For example, a ventilation tube having a larger lumen can be used for drainage purposes, as smaller lumen tubes block more easily with dried secretions. However, larger lumen grommets allow more water to pass through, increasing the risk of contamination or infection of the middle ear. Smaller lumen grommets may therefore be preferred for simple ventilation of the middle ear space. Increasing the width of the flanges 13, 14 will increase the time which the grommet is likely to remain in the eardrum, but the longer the grommet stays in the eardrum, the more likely it is to leave an unwanted hole in the drum. Smaller ventilation tubes also tend to be used in children, while the larger size ventilation tubes are generally used in adults.

In the illustrated embodiment, the ventilation tube has a lumen diameter ($d_l$) of approximately 1 mm, but the lumen diameter may typically vary between 0.5 mm and 1.5 mm. In the illustrated embodiment, the diameter ($d_f$) of the flanges 13, 14 is around 2 mm, but may typically vary between 1 mm and 3 mm. The inter-flange length (I) of the tubular member 11 of the illustrated embodiment is around 1.2 mm, but may typically vary between 1 mm and 1.5 mm.

The distance by which the tabs 15, 16 extend radially beyond the nominal diameter of their respective flanges will also vary, depending on the size of the grommet. For example, for smaller grommets, the tabs should be relatively larger and longer for ease of grasping and ease of locating in the eardrum, as described below. Conversely, for larger grommets, the tabs 15, 16 should be relatively smaller so that they do not unnecessarily interfere with migration and extrusion of the grommets. In the illustrated embodiment, each tab 15, 16 protrudes approximately 0.5 mm beyond the notional diameter of its flange. Hence, the transverse distance ($d_t$) between the tips of the tabs 15, 16 is around 3 mm. This distance may typically range between 1.5 mm and 4.5 mm.

The curvature of the arcuate edge of the nose portion of each tab 15, 16 is typically half the radius of the flanges 13, 14.

In use, either one of the tabs is grasped with a grasping forceps 17. The grasped tab becomes the proximal or posterior tab for insertion purposes. The other tab thereby becomes the distal or anterior tab and is inserted into an incision 18 formed in the tympanic membrane 19. The anterior tab and its flange are pushed through the incision 18 to thereby seat the ventilation tube in the membrane 19 with the flanges 13, 14 on either side thereof.

The abovedescribed ventilation tube has several advantages, including:

Either tab 15, 16 may be selected for use as the posterior tab to be grasped by the forceps 17, with the other tab serving as the anterior tab. Hence, unlike known ventilation tubes, the surgeon or theatre nurse need not manoeuvre the grommet in a tray to present a particular tab for grasping.

As the tabs 15, 16 are angled to the axis of the tubular member 11, the ventilation tube 10 is automatically positioned at the correct insertion angle, and the insertion of the ventilation tube in the tympanic membrane is facilitated. For example, if one of the tabs 15, 16 is grasped by the forceps 17, the other tab will be orientated at approximately the same angle as the forceps and its flange will be angled thereto, facilitating the insertion of the ventilation tube through the external auditory canal and into the tympanic membrane. The surgeon does not have to tilt or pivot the forceps unduly to manoeuvre the ventilation tube in place. At approximately 30° to their respective flanges, the tabs 15, 16 are at an appropriate angle both for grasping and insertion. This is particularly advantageous for surgeons who would otherwise require reading glasses in order to see the grommet and manoeuvre it to the correct angle. Where the surgeon uses a microscope to place the grommet, the glasses get in the way of the microscope eyepieces.

Although the tabs 15 are angled obliquely to the axis of the tubular member 11, the flanges 13, 14 are perpendicular to the tubular member, thereby providing better retention of the ventilation tube in the tympanic membrane.

The edges of the tabs 15, 16 are non-cutting, thereby avoiding the unnecessary trauma which may be caused by using prior art cutting edge tabs.

Although the tabs 15, 16 have blunt edges, the shape of the tabs facilitate the widening of the incision to suit the ventilation tube. When the rounded nose of the anterior tab is inserted into the slit in the tympanic membrane, the straight sides of the tab gradually expand the slit to the size of the associated flange to permit the flange to pass through the membrane, without overly widening the slit. Thus, the tab stretches the slit in an atraumatic manner only to the required extent.

As the ventilation tube is simple to use and reversible, it is easy to train operating theatre nurses to load the ventilation tube correctly onto grasping forceps.

The ventilation tube may be made in different sizes to suit particular applications.

The foregoing describes only one embodiment of the invention, and modifications which are obvious to those skilled in the art may be made thereto without departing from the scope of the invention as defined in the following claims.

The invention claimed is:

1. A ventilation tube suitable for insertion in an incised tympanic membrane, the ventilation tube comprising
   a tubular member having a longitudinal axis,
   a first flange located at one end of the tubular member and having a first tab extending therefrom,
   a second flange located at an opposite end of the tubular member and having a second tab extending therefrom, the second tab being located diametrically opposite to the first tab,
   wherein the first and second tabs are angled obliquely to the plane of their respective associated flanges by approximately equal angles but in opposite directions, the first and second tabs being generally parallel to each other,
   and wherein both of the first and second tabs have non-cutting edges suitable for insertion in an incision in the tympanic membrane, each tab having a pair of substantially straight edges that are tangential to its associated flange, and a nose portion with an arcuate edge extending between the substantially straight edges,
   and wherein either of the first and second tabs is able to be grasped by forceps in use, wherein the ventilation tube may be used reversibly.

2. A ventilation tube as claimed in claim 1, wherein the first and second flanges are perpendicular to the longitudinal axis of the tubular member, and the first and second tabs are angled obliquely to the longitudinal axis of the tubular member.

3. A ventilation tube as claimed in claim 2, wherein the first and second tabs are made of a stiff material.

4. A ventilation tube as claimed in claim 3, wherein each of the first and second tabs are angled between 15° and 60° to the plane of its respective associated flange.

5. A ventilation tube as claimed in claim 4, wherein each of the first and second tabs is angled at approximately 30° to the plane of its respective associated flange.

6. A ventilation tube as claimed in claim 1, wherein the first flange and first tab are substantially the same size and shape as the second flange and second tab, respectively.

7. A ventilation tube as claimed in claim 6, wherein the first and second tabs are integrally formed extensions of their respective associated flanges.

8. A ventilation tube as claimed in claim 1, wherein the tubular member has a bore having a diameter of between 0.5 mm and 1.5 mm, the tubular member has an inter-flange length of between 1 mm and 2 mm, the first and second flanges are generally circular and each have diameters between 1 mm and 3 mm, and the transverse distance between the nose portions of the first and second tabs is between 1.5 mm and 4.5 mm.

9. A ventilation tube suitable for insertion in a tympanic membrane, the ventilation tube comprising
   a tubular member having first and second generally circular flanges at opposite ends thereof orientated perpendicularly to an axis of the tubular member,
   the first flange having a first tab formed integrally therewith and angled obliquely to the plane of the first flange,
   the second flange having a second tab formed integrally therewith and angled obliquely to the plane of the second flange, the first and second tabs being located diametrically opposite,
   the first and second tabs being angled obliquely to the axis of the tubular member but parallel to each other,
   the first and second tabs being made of a stiff material, and wherein the first and second tabs have substantially identical shape to permit the ventilation tube to be used reversibly.

10. A ventilation tube as claimed in claim 9, wherein each tab has a pair of substantially straight non-cutting edges angled to each other and tangential to its associated flange, each tab further having a nose portion with an arcuate non-cuffing edge extending between the substantially straight edges.

11. A method of inserting a ventilation tube in a tympanic membrane, the tube having first and second flanges at opposite ends thereof which are perpendicular to the axis of the tube, a first tab integral with and angled to the first flange, and a second tab integral with and angled to the second flange, the first and second tabs being parallel, the method comprising:

forming an incision in the tympanic membrane,
grasping the first tab with forceps,
using the forceps to insert the second tab into the incision in a direction generally parallel to the orientation of the forceps, and
pushing the second tab and the second flange through the incision, such that the ventilation tube is seated in the membrane with the first flange and a second flange on opposite sides thereof.

12. A method as claimed in claim 11, wherein the incision has an initial length shorter than the diameter of the first flange, and pushing the second tab into the membrane further comprising using tangential edges of the first tab to stretch or widen the incision.

* * * * *